United States Patent [19]
Hochman

[11] 4,294,263
[45] Oct. 13, 1981

[54] SYSTEM FOR DETECTING PROBE DISLODGEMENT

[75] Inventor: Benjamin L. Hochman, Doylestown, Pa.

[73] Assignee: Air Shields, Inc., Hatboro, Pa.

[21] Appl. No.: 75,253

[22] Filed: Sep. 13, 1979

Related U.S. Application Data

[63] Continuation-in-part of Ser. No. 858,401, Dec. 7, 1977, abandoned.

[51] Int. Cl.³ .............................................. A61B 5/00
[52] U.S. Cl. .................................. 128/736; 73/343 R; 200/61.02; 200/DIG. 36; 340/600
[58] Field of Search ................ 128/1 B, 630, 639–641, 128/643, 644, 653, 664–667, 736, 687–690, 303.13, 908; 340/531, 555, 556, 573, 600; 200/61.02, DIG. 36; 73/343 R, 344

[56] References Cited

U.S. PATENT DOCUMENTS

| Re. 29,082 | 12/1976 | Schwarz | 340/555 |
| 2,737,644 | 3/1956 | Krieger | 340/600 |
| 2,976,419 | 3/1961 | Menke et al. | 340/600 X |
| 3,228,391 | 1/1966 | Fitter et al. | 128/666 |
| 3,300,770 | 1/1967 | Brousseau et al. | 340/600 X |
| 3,329,946 | 7/1967 | Robbins | 340/600 X |
| 3,930,249 | 12/1975 | Steck et al. | 340/600 X |

FOREIGN PATENT DOCUMENTS 2730574  2/1978  Fed. Rep. of Germany ...... 128/736

Primary Examiner—Lee S. Cohen
Attorney, Agent, or Firm—Weiser, Stapler & Spivak

[57] ABSTRACT

A probe having a contact surface adapted to be placed on a body surface to monitor or control a body function. When the probe is dislodged from the body, an increased radiation level impinging on the contact surface is sensed and an indication of probe dislodgement is provided.

23 Claims, 5 Drawing Figures

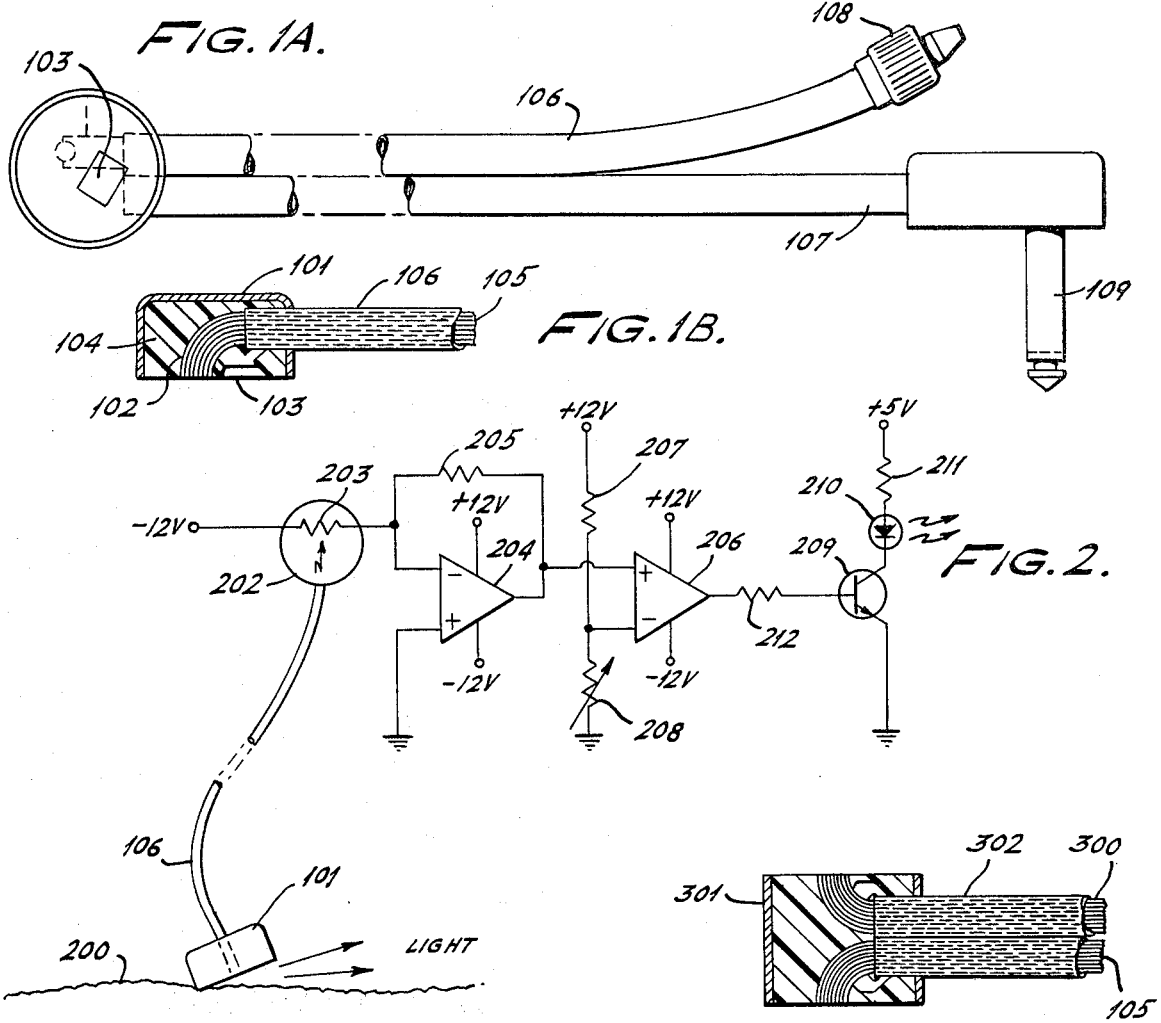
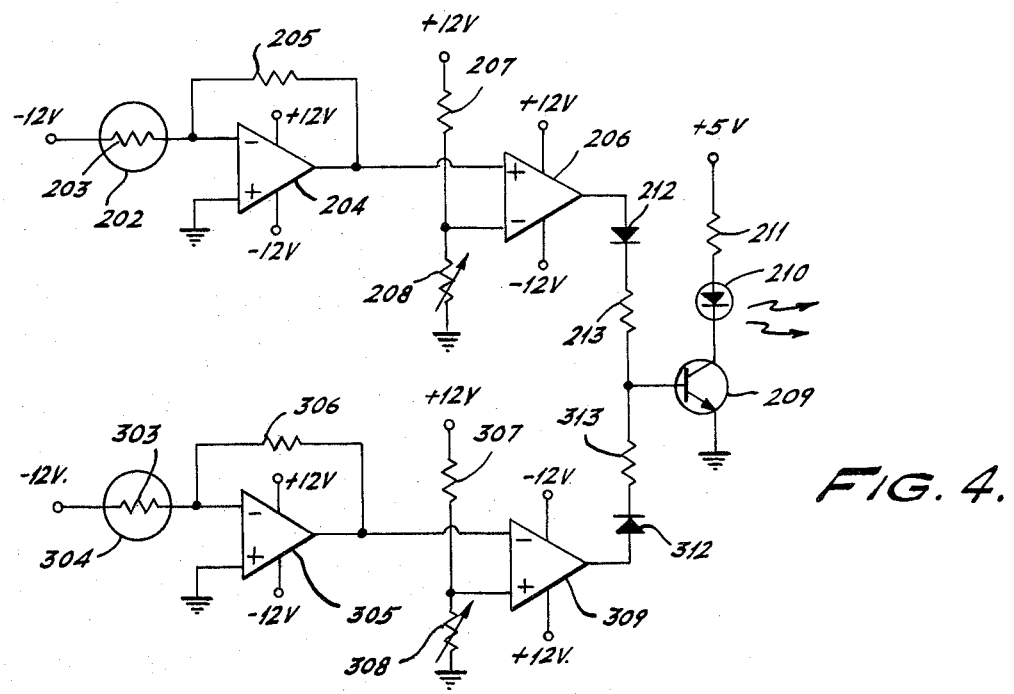

SYSTEM FOR DETECTING PROBE DISLODGEMENT

BACKGROUND OF INVENTION

This application is a continuation-inpart of application Ser. No. 858,401 filed Dec. 7, 1977, now abandoned.

This invention relates to skin contact probes, and more particularly to apparatus for detecting dislodgement of such probes. Although the invention will be described in connection with a probe having means for sensing body temperature, it will be apparent that the invention has broader application. The invention may be extended to probes which monitor other body functions and to probes which control or influence a body state or condition.

As an example, several devices, in common use, provide thermal environmental control by positioning temperature probes which are intended to be maintained in intimate contact with the skin and by utilizing such probes to control operation of a heater for incubators and radiant warmers. Typically, such probes involve a thermoelectric transducer mounted on a skin contact surface. Electrical signals from the transducer are utilized for heater control. In such instances, it is essential to maintain intimate contact between the probe and the skin, and particularly to maintain contact with the skin and the rather sensitive thermoelectric transducer. Should the probe become completely dislodged, there is the possibility of having it contact a hot or cold surface, with consequent derangement of the thermal environment. Even a small discontinuity between probe and skin, short of total dislodgement, can work adversely to proper control of the thermal environment. Furthermore, it is important to know when a system, provided for identifying probe dislodgement, is rendered ineffective to perform this function.

It is an object of the present invention to provide apparatus for detecting dislodgement of skin contact probes, and more particularly to detect even rather slight discontinuities between the probe and the skin.

It is a more particular object of the present invention to provide apparatus which senses probe dislodgement based on the receipt of ambient light, or radiation from specific sources, at the skin contact surface of the probe when mounted on the skin.

It is a still further object that the apparatus for sensing probe dislodgement by light reception being capable of discriminating between light associated with the dislodgement, and light which arrives through skin translucence during adequate contact, and furthermore that it do so independently of the pigmentation of the skin of the subject.

Yet another object of the present invention is to provide a probe which develops an indication when the probe is covered and thereby prevented from sensing dislodgement.

SUMMARY OF THE INVENTION

The present invention senses increased radiation levels attendant to dislodgement of a contact probe from a skin surface with which it is placed in contact. Transducer means having a light receiving portion located in the skin contact surface of the probe sense the increased radiation level impinging on the probe contact surface when the probe is dislodged and a radiation signal is developed representative of the radiation level impinging upon the contact surface. When a threshold is exceeded, indicating dislodgement, an alarm circuit is energized. The alarm threshold may be adjusted to meet varying conditions of ambient light, skin pigmentation and the like.

DESCRIPTION OF THE DRAWINGS

FIGS. 1a and 1b show, respectively, a bottom view and a side cutaway view of a probe embodying the principles of the present invention;

FIG. 2 shows a schematic circuit for detecting and displaying probe dislodgement conditions;

FIG. 3 is a side cutaway view of another embodiment of a probe embodying the principles of the present invention; and FIG. 4 shows a schematic circuit useful with the probe of FIG. 3 for detecting and displaying probe dislodgement conditions.

DETAILED DESCRIPTION

Referring first to FIGS. 1a and 1b, there is shown a skin temperature probe embodying the principles of the present invention. In the Figures, a thermistor 103 is employed, as is conventional in thermal sensing skin contact probes. Electrical signals from the thermistor 103, corresponding to skin temperature changes, are coupled via cable 107 and jack 109 to the heater controls, there to enable appropriate changes in the thermal environment to correspondingly increase or decrease the skin temperature of the subject. The probe is defined by an outer housing 101, which is shown to have a generally cylindrical configuration, but which, it will be appreciated, may vary in accordance with the characteristics of the subject and the needs of the designer. The lower, or skin contact surface of the probe, carries not only the thermistor 103, but also the end of a fiber-optic bundle 105, suitably optically prepared for receipt and conveyance of impinging light, be it ambient light or light from a specific source.

Fiber-optic bundle 105 passes through a rigid elbow 102 directing the bundle toward and through the outside of the housing 101. A potting compound 104, such as epoxy or the like, not only holds the fiber-optic bundle 105 and the thermistor 103 in place within the housing 101, but also defines generally the skin contact surface thereof and holds the position of the optically prepared end of fiber-optic bundle 105 and the thermistor 103 thereon. A hollow conduit 106 encloses the fiber-optic bundle 105 between the probe, monitor and alarm circuitry described below. A suitable connector 108 is provided at the free end of conduit 106.

In the embodiment shown, FIGS. 1a and 1b, the fiber-optic bundle 105 is maintained clustered together, generally at the center of the skin contact surface, and in relatively close proximity to the thermistor 103. The housing 101 and the conduit 106 are opaque, whereby ambient light will not impinge on the sides of the fiber-optic bundle 105, and the only light in bundle 105 will arrive from the input end of the probe-skin contact surface. Likewise, loss of light in transmission along bundle 105 is thereby prevented.

In an alternative embodiment, respective portions of the optical fibers 105 may be arrayed at disparate points on the skin contact surface, for example at the periphery thereof or surrounding the thermistor 103. In such event, the elbow casing 102 may not be required, with the respective fibers converging into a bundle near the exit from the housing 101, thence traversing the interior of conduit 106.

Any of the embodiments of the present invention may employ an extensive variety of configurations for the probe 101, including for example, the entire probe structure, corresponding to housing 101 and potting compound 104 may be fabricated of an integral molding, about the optical interface at the termination of bundle 105, and the thermistor 103. Many commercially available materials are suitable for such an application, polyurethane rubber casting compound being one of them. Moreover, a separate light source may be provided in proximity of the probe 101 to provide a source of light for the functioning of the monitor and alarm of the invention especially when there is an absence of ambient light. Alternatively, the separate light source may be remote from the probe and the light conducted to the probe through a fiber-optic bundle.

As shown in FIG. 2, the probe 101 may be disposed against the skin 200 of a subject in a dislodgement position whereby ambient light impinges on the skin contact surface of the probe. Not shown is the apparatus for holding the probe in place. This may involve tape, belts, straps, or the like. In such an event, light received at the optical interface as a result of dislodgement is conveyed via the fiber-optic bundle 105 within conduit 106 to an optical detector 203. The circle identified by reference number 202 represents a receptacle which receives and engages connector 108 of conduit 106.

Numerous types of optical detectors 203 are available, each with its own respective operational characteristics. The preferred embodiment herein utilizes a detector 203 having a preference for sensitivity, rather than operational speed. Generally, all types of commercially available photosensors function within a time responsiveness range satisfactory to render a timely alarm in response to the light impinging on the probe bundle 105 upon dislodgement. However, some photoelectric transducers possess sensitivity characteristics which are preferable to others for purposes of the present invention. In a preferred embodiment, the photosensor 203 is a photoconductive cell of the cadium sulfide type, for example, those available under the commercial designation "Clairex C1 909L" cell. It is to be understood, however, that depending on the system to which the invention is applied, and the particular sensitivity/responsiveness constraints thereon, the photodetector 203 may also be embodied as photo-Darlington transistor, a PIN transistor, a PIN silicon photo diode, photovoltaic cell, or the like.

The photodetector 203 is connected to a −12 volt supply. A current change produced by a change in the conductivity of the photodetector 203 when energized by light from the fiber-optic bundle is coupled to the inverting input of an amplifier 204, the non-inverting input of which is held at ground. Amplifier 204 is arranged with resistor 205 in a feedback configuration to the inverting input. The amplifier 204 fulfills the function of a linear detection of current from photosensor 203, and therefore preferably involves strong current sensing capabilities with negligible bias currents over the operating temperature involved. In a preferred embodiment, amplifier 204 is implemented by a high input impedance operational amplifier such as those having junction effect transistor (JFET) input stages, for example those available under the commercial designation "National LF355" integrated circuits.

The output of amplifier 204 is coupled to the non-inverting input of a comparator-amplifier 206 which functions as a threshold circuit. The inverting input of amplifier 206 is coupled to the central point of a voltage divider comprising resistors 207 and 208 connected between a +12 voltage supply and ground. Hence, the signal at the non-inverting input of amplifier 206 will cause amplifier 206 to go positive depending upon input signal amplitude relative to the threshold voltage from divider 207 and 208. The threshold voltage is set to represent a predetermined light level corresponding to the level of background light reaching the end of fiber-optic bundle 105 when the skin contact surface of the probe is in contact with the skin. Amplifier 206 is the type commercially available under the trade designation "LM301".

Comparator-amplifier 206 has its output coupled through a resistor 212 to the base of a transistor 209, which has a light emitting diode 210 in its collector circuit. The light emitting diode 210 is connected in series with a resistor 211 between a +5 volt supply and the collector of the transistor 209 while the emitter of this transistor 209 is tied to ground.

When the voltage from amplifier 204 to comparator 206 exceeds the threshold voltage established by the divider 207 and 208 transistor 209 is turned on, and diode 210 is switched into the conducting state. The light emitted serves to alarm the condition of dislodgement, indicating to the operator of the system that the probe 101 has become dislodged from the skin 200.

Resistor 208 is shown as a variable resistor, thereby affording an adjustment facility to the threshold of comparator 206, in order to account for anticipated ranges of ambient light, circuit sensitivity-parameters, and skin pigmentation and translucence characteristics. Depending upon the application desired, the resistor 208 may be present during a calibration process, or may be variable in accordance with the needs of the operator.

It is to be understood that audible alarm systems may be utilized in substitution for, or in conjunction with the light emitting diode 210.

The invention operates wherein, should the probe 101 become partially dislodged from the skin 200, ambient light will impinge on the skin contact surface of the probe, and will be conveyed by the fiber-optic bundle 105 within conduit 106 to the photosensor 203. An electrical signal is produced thereby, processed at amplifier 204 and comparator 206, and the alarm diode 210 is energized upon the activation of transistor 209.

FIG. 3 shows a second embodiment of a probe constructed in accordance with the present invention and provided with means for sensing when the probe is covered so as to be shielded from sources of light and rendered ineffective. In use, a body probe may become covered by a blanket, bandage or piece of equipment. When this occurs, an optical sensing technique for detecting probe dislodgement will not function properly, if at all, if the light sensor is shielded from the ambient light or a specific source of light. In the FIG. 3 probe, a second fiber-optic bundle 300 is provided which opens into the top surface of probe housing 301. A hollow conduit 302 encloses fiber-optic bundle 300 between the probe and the alarm circuitry shown in FIG. 4.

Under normal operating conditions, fiber-optic bundle 105 transmits no light or very little light while the contact surface of housing 301 is in contact with the skin. At the same time fiber-optic bundle 300 transmits the light impinging upon the top surface of housing 301.

If the probe becomes covered by a blanket or the like, the light level transmitted by fiber-optic bundle 300 drops significantly to the level of light which penetrates the covering.

Much of the circuit shown in FIG. 4 corresponds to the circuit of FIG. 2 and like components have been given the same reference numerals. The lower branch of the FIG. 4 circuit, added to develop an alarm indication when the probe is shielded from its light source, functions in a manner generally similar to the upper branch.

Light received at the top of probe housing 301 is conveyed via fiber-optic bundle 300 within conduit 302 to an optical detector 303. The circle identified by reference number 304 represents a receptacle which receives and engages the free end of conduit 302.

Optical detector 303 is connected to a −12 volt supply. A circuit change produced by a change in the conductivity of optical detector 303 when energized by light from the fiber-optic bundle is coupled to the inverting input of an amplifier 305, the non-inverting input of which is held at ground. Amplifier 305 is arranged with a resistor 306 in a feedback configuration to the inverting input. Amplifier 305 preferably is similar in construction and operation to amplifier 204.

The output of amplifier 305 is coupled to the inverting input of a comparator-amplifier 309 which functions as a threshold circuit. The non-inverting input of amplifier 309 is coupled to the central point of a voltage divider comprising resistors 307 and 308 connected between a +12 volt supply and ground. With this arrangement, a signal at the inverting input of amplifier 306 will drive the amplifier output negative. This corresponds to light being detected by optical detector 303 which indicates that the probe is not covered and operating as expected. When the amplitude of the signal at the inverting input of amplifier 309 falls below the threshold voltage established by divider 307 and 308, amplifier 309 operates to develop a positive output signal. This corresponds to little, if any, light being detected by optical detector 303 which indicates that the probe is covered or shielded from light. The threshold voltage at the junction of resistors 307 and 308 is set to represent a predetermined light level corresponding to the level of light impinging upon the end of fiber-optic bundle 300 when the probe is uncovered. This threshold voltage may be set so that more than only a slight decrease in light level impinging upon the top surface of the probe is required to operate amplifier 309. The setting of resistor 308 is determined by the degree of decrease in light level for which it is desired to set off the alarm. Amplifier 309 preferably is similar in construction and operation to amplifier 206.

The output of comparator-amplifier 206 is coupled to the base of transistor 209 through a diode 212 and a resistor 213. The output of comparator-amplifier 309 is coupled to the base of transistor 209 through a diode 312 and a resistor 313. The arrangement is such that when either or both comparator-amplifier 206 and comparator-amplifier 309 develop a positive output signal, transistor 209 conducts and light emitting diode 210 is energized. In particular, amplifier 309 develops a positive output signal whenever the probe is covered and the signal at the inverting input of amplifier 306 is below the threshold amplitude. Thus, regardless of the output from amplifier 206, light emitting diode 210 will be energized whenever the probe is covered. If the probe remains uncovered, but becomes dislodged from the body, an input current increase to the non-inverting input of amplifier 206 will produce an output which causes light emitting diode 210 to become energized. Whether the alarm is set off because of probe dislodgement or probe covering, the system succeeds in catching the attention of someone who can determine which of the two possibilities caused the alarm.

Although the invention, as described, contemplates the detection of ambient light, detectors which are selectively responsive to only a portion of the light spectrum (e.g. infrared) may be employed and, likewise, the radiation source may be of a more narrow bandwidth.

As stated previously, the present invention has broader application than a skin contact temperature probe. The invention may be applied to other body surface probes which monitor or control other body functions or to probes which penetrate the body. For example, the dislodgement or partial withdrawal of an intravenous feed needle, designed to have a contact surface, may be detected by incorporating the principles of the present invention.

While the embodiments of the probe illustrated in FIGS. 1a, 1b and 3 show the use of fiber-optic bundles which transmit light to a distant alarm circuit at which photosensors convert the light to electrical signals, or other electro-optical techniques may be employed in practicing the present invention. For example, photocells may be located in the probe contact surface and in the upper housing surface to receive the light and develop electrical signals which are transmitted to the distant alarm circuit.

The foregoing has set forth exemplary and preferred embodiments of the present invention. It will be understood, however, that numerous alternative embodiments will occur to those of ordinary skin in the art without departure from the spirit or scope of the present invention.

What is claimed:

1. Apparatus for sensing skin contact probe dislodgement, comprising:
    (a) housing means defining a skin contact surface for said probe;
    (b) photoreceptive means located on said skin contact surface of said housing means;
    (c) alarm means energized by reception by said photoreceptive means of light, said light having an intensity exceeding a predetermined level, said alarm means being placed a distance away from said housing means; and
    (d) photo transmitting means extending out from said housing means for connecting said photoreceptive means and said distant light receptive alarm means.

2. Apparatus as described in claim 1 wherein said alarm means comprises:
    a transducer means for converting light, received from said photoreceptive means, to an electrical signal; and
    circuit means for detecting said electrical signal and for displaying a condition corresponding to a change in surface contact.

3. Apparatus as described in claim 2 wherein said phototransmitting means comprises: a fiber-optic bundle extending to said transducer means from said photoreceptive means; and an opaque conduit surrounding said fiber-optic bundle.

4. Apparatus as described in claim 3 wherein said photoreceptive means includes:
    an optically polished fiber-optic end.

5. Apparatus as described in claim 4 wherein said circuit means includes:
a threshold detection circuit, responsive to said transducer means electrical signal, said threshold corresponding to the level of background light reaching said photoreceptive means when there is intimate contact between the patient's skin and said skin contact surface; and
light emitting alarm means energized by said threshold circuit.

6. Apparatus for sensing probe dislodgement comprising:
a probe housing having a contact surface adapted for contact with a body and also having means for carrying a probe;
transducer means having a radiation receiving portion located in said contact surface for (1) sensing an increased radiation level impinging upon said contact surface when said probe housing is dislodged from said body and said contact surface is exposed to said increased radiation level, and (2) developing a radiation signal representative of the radiation level impinging upon said contact surface; means for supplying a threshold signal representative of a predetermined radiation level less than said increased radiation level impinging upon said contact surface when said probe housing is dislodged from said body; and
alarm means responsive to said radiation signal and said threshold signal for developing an indication when said radiation level impinging upon said contact surface exceeds said predetermined radiation level.

7. Apparatus according to claim 6 wherein said predetermined radiation level corresponds to the level of background radiation reaching said radiation receiving portion when said contact surface is in contact with said body.

8. Apparatus according to claim 7 wherein said alarm means include a light emitting device which is energized when said radiation level impinging upon said contact surface exceeds said predetermined level.

9. Apparatus according to claim 6 wherein said transducer means include light responsive means for sensing light impinging upon said contact surface and developing a light signal representative of the light level impinging upon said contact surface.

10. Apparatus according to claim 9 wherein said light responsive means include (1) a fiber-optic bundle having an input end in said contact surface and an output end distant from said contact surface, and (2) a photodetector positioned at said output end of said fiber-optic bundle and responsive to light transmitted from said contact surface by said fiber-optic bundle.

11. Apparatus according to claim 6 wherein said apparatus also includes a thermistor embedded in said probe housing for sensing the temperature of said body and developing a signal representative of said temperature and means for transmitting said temperature signal to a distant location.

12. A probe for sensing a body function comprising:
a probe housing having a contact surface adapted to contact with a body;
sensor means located in said contact surface and responsive to said body function for developing an output representative of said body function;
radiation receiving means located in said contact surface for sensing an increased radiation level impinging upon said contact surface when said probe housing is dislodged from said body and said contact surface is exposed to said increased radiation level and for developing an output representative of said increased radiation level; and
means emanating from said housing for transmitting said outputs of said sensor means and said radiation receiving means to a distant location.

13. A probe according to claim 12 wherein said sensor means is a thermistor which develops a signal representative of the temperature of said body and said transmitting means include electrical connection means for conducting said signal to said distant location.

14. A probe according to claim 13 wherein said transmitting means further include a fiber-optic bundle which transmits said radiation impinging upon said contact surface to said distant location.

15. Apparatus for indicating the dislodgement of an article from a body surface, said apparatus comprising:
an article having a contact surface adapted for contact with a body surface and a second surface removed from said contact surface;
first transducer means having a radiation receiving portion located in said contact surface for (1) sensing an increased radiation level impinging upon said contact surface when said article is dislodged from said body surface and said contact surface is exposed to said increased radiation level, and (2) developing a first radiation signal representative of the radiation level impinging upon said contact surface;
second transducer means having a radiation receiving portion located in said second surface for (1) sensing a decreased radiation level impinging upon said second surface when said article is covered and said second surface is exposed to said decreased radiation level, and (2) developing a second radiation signal representative of the radiation level impinging upon said second surface;
means for supplying a first threshold signal representative of a first predetermined radiation level less than said increased radiation level impinging upon said contact surface when said article is dislodged from said body;
means for supplying a second threshold signal representative of a second predetermined radiation level greater than said decreased radiation level impinging upon said second surface when said article is covered; and
alarm means responsive to said first and second radiation signals and said first and second threshold signals for developing an indication where said radiation level impinging upon said contact surface exceeds said predetermined first radiation level or said radiation level impinging upon said second surface falls below said predetermined second radiation level.

16. Apparatus according to claim 15 wherein said predetermined first radiation level corresponds to the level of background radiation reaching said radiation receiving portion of said first transducer means and said predetermined second radiation level corresponds to the level of radiation impinging upon said second surface when said article is uncovered.

17. Apparatus according to claim 16 wherein said alarm means include a light emitting device which is energized when said radiation level impinging upon said contact surface exceeds said background radiation or said radiation level impinging upon said second surface falls below the level or radiation impinging upon said second surface when said article is uncovered.

18. Apparatus according to claim 17 wherein said second surface is on the opposite side of said article from said contact surface.

19. Apparatus according to claim 18 wherein said first and second transducer means include light responsive means for sensing light impinging upon said contact surface and said second surface.

20. Apparatus according to claim 19 wherein (1) said first transducer means include (a) a first fiber-optic bundle having an input end on said contact surface and an output end distant from said contact surface, and (b) a first photo-detector positioned at said output end of said first fiber-optic bundle and responsive to light transmitted from said contact surface by said first fiber-optic bundle; and (2) said second transducer means include (a) a second fiber-optic bundle having an input end in said second surface and an output end distant from said second surface, and (b) a second photo-detector positioned at said output end of said second fiber-optic bundle and responsive to light transmitted from said second surface by said second fiber-optic bundle.

21. A probe for sensing a body function comprising: a probe housing having a contact surface adapted for contact with a body and a second surface removed from said contact surface; sensor means located in said contact surface and responsive to said body function for developing an output representative of said body function; first radiation receiving means located in said contact surface for sensing an increased radiation level impinging upon said contact surface when said probe housing is dislodged from said body and said contact surface is exposed to said increased radiation level and for developing an output representative of said increased radiation level;

second radiation receiving means located in said second surface for sensing a decreased radiation level impinging upon said second surface when said probe housing is covered and said second surface is exposed to said decreased radiation level and for developing an output representative of said decreased radiation level; and means emanating from said housing for transmitting said outputs of said sensor means and said first and second radiation receiving means to a distant location.

22. A probe according to claim 21 wherein said sensor means is a thermistor which develops a signal representative of the temperature of said body and said transmitting means include electrical connection means for conducting said signal to said distant location.

23. A probe according to claim 22 wherein said transmitting means further include first and second fiber-optic bundles which transmit said radiation impinging upon said contact surface and said second surface to said distant location.

* * * * *